United States Patent

Wang

Patent Number: 5,093,500

Date of Patent: Mar. 3, 1992

[54] SPIRODILACTAM BISIMIDES

[75] Inventor: Pen-Chung Wang, Houston, Tex.

[73] Assignee: Shell Oil Company, Houston, Tex.

[21] Appl. No.: 599,188

[22] Filed: Oct. 17, 1990

[51] Int. Cl.$^5$ .................. C07D 209/56; C07D 403/04
[52] U.S. Cl. ...................................... 548/410; 548/411
[58] Field of Search ................................ 548/410, 411

[56] References Cited

U.S. PATENT DOCUMENTS 3,740,378  6/1973  Crivello ............................... 260/78
4,472,565  9/1984  Ryang ................................... 528/26
4,968,770  11/1990  Wang ................................. 528/229

Primary Examiner—Mary C. Lee
Assistant Examiner—John Peabody

[57] ABSTRACT

A 1,6-diaza[4.4]spirodilactam monomer or oligomer having an aliphatically-unsaturated imido-containing substituent on each terminal spiro ring nitrogen atom and cured products thereof.

8 Claims, No Drawings

SPIRODILACTAM BISIMIDES

FIELD OF THE INVENTION

This invention relates to a novel class of imido-substituted spirodilactams. More particularly, it relates to novel 1,6-diaza[4.4] spirodilactams having an aliphatically-unsaturated imido-containing substituent on each terminal spiro ring nitrogen atom and cured products thereof.

BACKGROUND OF THE INVENTION

The reaction of aliphatically-unsaturated imido-amino compounds with dibasic acids or equivalent compounds is well known in the art. In general, the typical product from such a reaction is a monomer, as in U.S. Pat. No. 4,472,565, or to make polymers, as in U.S. Pat. No. 3,740,378.

A class of compounds that functions in some ways similar to dicarboxylic acids is the class of 1,6-dioxa[4.4]spirodilactones. The simplest member of the series, 1,6-dioxaspiro[4.4]nonane-2,7-dione, is known and has been prepared, among several procedures, by the process of Pariza et al., *Synthetic Communications*, Vol. 13(3), pp. 243-254 (1983). These spirodilactones have demonstrated utility as an epoxy curing agent to produce cured compositions which do not shrink during the curing process. It is likely that this reaction, as well as other reactions of such spirodilactones, produce a ring-opened product. See, for example, the above Pariza et al. article and Cowsar, U.S. Pat. No. 4,064,086. A reaction of the spirodilactones, or of 4-oxoheptanedioic acid compounds, which results in a cyclic product is shown by U.S. Pat. No. 4,939,270. The patent discloses the reaction of the acidic materials with diamines to make certain diamines incorporating a spirodilactam moiety. Reaction of these acidic compounds with a stoichiometric or excess amount of a primary diamine wherein the two amino groups are not on adjacent carbon atoms produces polymeric polyamides which incorporate spirodilactam moieties as shown by allowed copending U.S. Pat. application Ser. No. 245,432, filed Sept. 16, 1988, now U.S. Pat. No. 4,968,770.

It would be of advantage to provide a novel class of aliphatically-unsaturated bisimides incorporating spirodilactam moieties which are monomeric, oligomer or cured products therefrom.

SUMMARY OF THE INVENTION

The present invention provides a novel class of difunctional end-capped 1,6-diaza[4.4]spirodilactams or oligomers having an aliphatically-unsaturated imido-containing substituent on each spiro ring nitrogen atom and to cured products from either. More particularly, the invention relates to reaction of a spirodilactam precursor selected from 4-oxoheptanedioic acid compounds or 1,6-dioxa[4.4]spirodilactones with an aliphatically-unsaturated imido-primary amine compound, in a controlled reaction mixture ratio, to produce a monomeric or oligomeric 1,6-diaza[4.4]spirodilactam, having an aliphatically-unsaturated imido-containing substituent on each terminal spiro ring nitrogen atom.

SPIRODILACTAM BISIMIDES

The spirodilactam bisimide compound is produced by reaction of an appropriate aliphatically-unsaturated imido-primary amine compound, i.e., an organic compound having one primary amino group ($-NH_2$ group) and an aliphatically-unsaturated imido group, with a spirodilactam precursor.

In one embodiment of the invention, the spirodilactam precursor is a ketodicarboxylic acid compound of up to 30 carbon atoms having two carbon atoms between the keto group and each carboxy function. In other terms, the spirodilactam precursor of this modification is a 4-oxoheptanedioic acid compound.

Although a variety of such ketodiacids having a variety of substituents in addition to the keto group and the acid functions are useful, the preferred 4-oxoheptanedioic acid compounds are those compounds of up to 30 carbon atoms inclusive which are represented by the formula I

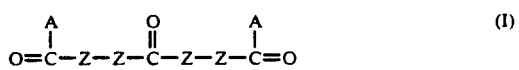

$$O=C-Z-Z-C-Z-Z-C=O \quad \text{(I)}$$

wherein A independently is hydroxy, alkoxy, preferably lower alkoxy of up to 4 carbon atoms inclusive, or halo, preferably the middle halogens, chloro or bromo, and Z independently is $>C(Z')_2$ in which $Z'$ independently is hydrogen, lower alkyl of up to 4 carbon atoms inclusive, preferably methyl, halo, preferably the lower halogens fluoro or chloro, or aryl, preferably phenyl, or Z is such that two adjacent Z groups taken together form a ring system $Z''$ of from 5 to 7 ring atoms, up to two of which are heteroatoms selected from nitrogen, oxygen or sulfur with the remainder of the ring atoms being carbon atoms, there being up to 15 carbon atoms in each $Z''$, two of which form a bridge between the carbon atoms connected by the adjacent Z groups.

In one embodiment employing the spirodilactam precursor of formula I, the ketodiacid is an acyclic 4-oxoheptanedioic acid compound wherein each Z is not a part of a fused cyclic substituent, i.e., Z is $>C(Z')_2$. In one such embodiment, largely because of a particularly convenient method of producing the spirodilactam precursor, the 4-oxoheptanedioic acid compound has at least one hydrogen present on each carbon atom adjacent to a carboxy function, that is, at least one $Z'$ present on each carbon atom adjacent to a carboxy function is hydrogen. Such 4-oxoheptanedioic acid compounds are represented by the formula Ia

$$O=C-CHZ'-C(Z')_2-C-C(Z')_2-CHZ'-C=O \quad \text{(Ia)}$$

wherein A and $Z'$ have the previously stated meanings. Such 4-oxoheptanedioic acid compounds include 4-oxoheptanedioic acid, dimethyl 4-oxoheptanedioate, 2,6-dimethyl-4-oxoheptanedioic acid, 2,3,5,6-tetramethyl-4-oxoheptanedioyl chloride, di-n-propyl 2,6-di-n-butyl-4-oxoheptandioate and 6-carboxymethyl-2,3,5,5-tetramethyl-4-oxohexanoic acid. The preferred compounds of the above formula Ia are those wherein $Z'$ is hydrogen or methyl, particularly hydrogen, and A is hydroxy or alkoxy, particularly hydroxy.

These ketodiacids are known compounds or are produced by known methods, but the esters of the above formula Ia are produced by the reaction of formaldehyde and an ethylenically unsaturated carboxylic acid ester such as methyl acrylate, ethyl methacrylate, butyl acrylate or methyl crotonate. The reaction is conducted in the presence of a catalyst system which comprises a thiazolium salt and a tertiary amine and produces the dialkyl 4-oxoheptanedioate derivative in good yield. This process is described in more detail and claimed in U.S. Pat. No. 4,800,231 incorporated herein by reference. Conversion of the esters thereby obtained to the acids or the acid halides is by known methods.

In a second embodiment of the ketodiacid compound as a spirodilactam precursor, the 4-ketodiacid incorporates fused ring cyclic substituents between the keto group and each carboxy function, i.e., the adjacent Z groups are Z". Such diacid compounds are represented by the formula Ib

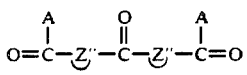

(Ib)

wherein A and Z" have the previously stated meanings. Illustrative of these cyclic ketodiacid compounds are di(2-carboxycyclohexyl) ketone, di(2-carboxyphenyl) ketone, di(2-carbopropoxycyclo-4-pentenyl) ketone, di(2-chlorocarbonylphenyl) ketone, di(2-carboxypyridyl) ketone, 2-carboxyphenyl N-methyl-3-carboxy-3-pyrryl ketone, di(3-carboxy-2-morpholyl) ketone and di(2-carboxy-3-chlorophenyl) ketone. The preferred cyclic ketodiacid compounds of formula Ib are those wherein each Z" is a ring system of from 5 to 6 ring atoms and up to one nitrogen atom, particularly benzo.

The cyclic ketodiacid compounds of formula Ib are known compounds or are produced by known methods, for example the method of Conover et al., U.S. Pat. No. 1,999,181 or by the method of Cava et al., J. Am. Chem. Soc., 77, 6022(1955).

In yet another embodiment of the ketodiacid compound as the spirodilactam precursor, the ketodiacid compound incorporates one cyclic moiety with the remainder of the Z moieties being acyclic i.e., the compounds of the formula Ic

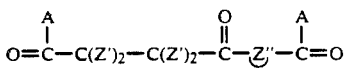

(Ic)

wherein A, Z' and Z" have the previously stated meanings. Such ketodiacid compounds of one cyclic substituent are illustrated by 3-(2-carboxybenzoyl) propionic acid, 3-(2-carbomethoxy-2-pyridyloyl)-2-ethylpropionic acid, ethyl 3-(2-carbethoxybenzoyl)propionate and 3-(2-carboxy-4-methylbenzoyl)butyl chloride. The ketodiacids of formula Ic are known compounds or are produced by known methods. For example, 2-carbomethoxybenzaldehyde reacts with methyl acrylate according to the general teachings of U.S. Pat. No. 4,800,231 to produce 3-(2-carbomethoxybenzoyl)propionate.

In a second embodiment of the invention, the spirodilactam precursor is a 1,6-dioxaspiro[4.4]nonane-2,7-dione compound of up to 30 carbon atoms wherein the spiro ring system is substituted with hydrogen or other monovalent groups or incorporates fused ring substituents which include the 3- and 4- spiro ring positions and/or the 8- and 9- spiro ring positions of the spiro ring system. One class of such spirodilactones is represented by the formula II

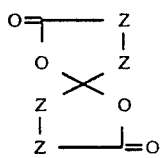

(II)

wherein Z has the previously stated meaning. In the embodiment of these spirodilactone spirodilactam precursors of the above formula II wherein each Z is $>C(Z')_2$, the spirodilactone is represented by the formula IIa

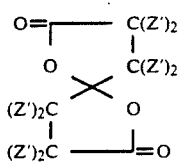

(IIa)

wherein Z' has the previously stated meaning. Illustrative of such spirodilactones are 1,6-dioxaspiro[4.4]nonane -2,7-dione, 3,8-dimethyl-1,6-dioxaspiro[4.4]nonane-2,7-dione, 3,4,8,9-tetramethyl-1,6-dioxaspiro[4.4]nonane-2,7-dione, 3,3,8,8-tetramethyl-1,6-dioxaspiro[4.4]nonane -2,7-dione, 3,3,4,4,8,8,9,9-octamethyl-1,6-diazaspiro[4.4]nonane-2,7-dione and 3,4,8,9-tetrafluoro-1,6-diazaspiro[4.4]nonane-2,7-dione. The preferred spirodilactones of formula IIa are those wherein at least one Z' of each Z'-substituted carbon atom is hydrogen. The compounds of formula IIa are known compounds or are produced by known methods such as by the process of the above Pariza et al. article, incorporated herein by reference.

In the embidiment of the spirodilactam precursors of formula II which incorporate a fused cyclic substituent as a part of each of the two rings of the spiro ring system, the spirodilactone are represented by the formula IIb

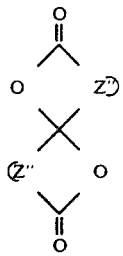

(IIb)

wherein Z" has the previously stated meaning. Typical compounds of this formula IIb are 3,4,8,9-dibenzo-1,6-dioxaspiro[4.4]nonane-2,7-dione, 3,4,8,9-dibenzo-1,6-dioxaspiro[4.4]nonane-2,7-dione, 3,4,8,9-di(cyclopentano)-1,6-dioxaspiro[4.4]nonane-2,7-dione, 3,4,8,9-di(-methylbenzo)-1,6-dioxaspiro[4.4]nonane-2,7-dione and 3,4,8,9-di(pyrido)-1,6-dioxaspiro[4.4]nonane-2,7-dione. These spirodilactones are known compounds or are produced by known methods such as, for example, the process of the above Cava et al. article or by the general process of Conover et al., U.S. Pat. No. 1,999,181.

In another embodiment of a spirodilactone as spirodilactam precursor, a cyclic substituent is fused to one spiro ring and the other spiro ring is free of fused ring substituents. Such spirodilactones are represented by the formula IIc

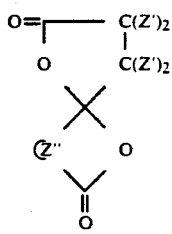

wherein Z' and Z" have the previously stated meaning. Such spirodilactones are illustrated by 3-methyl-8,9-benzo-1,6-dioxaspiro[4.4]nonane-2,7-dione, 3,4-benzo-1,6-dioxaspiro[4.4]nonane-2,7-dione and 3,3,4,4-tetramethyl-8,9-morpholo-1,6-dioxaspiro[4.4]nonane-2,7-dione. The spirodilactones of the above formula IIc are produced by known methods, for example, by the dehydration of the corresponding ketoacid. By way of illustration, 3,4-benzo-1,6-dioxaspiro[4.4]nonane-2,7-dione is produced by dehydration of 3-(2-carboxybenzoyl)-propionic acid through application of heat.

In general, the preferred spirodilactones to be employed as spirodilactam precursors are hydrocarbyl except for the oxygen atoms of the lactone moieties, particularly those spirodilactones which are free of fused ring substituents (formula IIa) or which have a fused ring substituent on each spiro ring (formula IIb). The compound 1,6-dioxaspiro[4.4]nonane-2,7-dione is an especially preferred member of the former class while 3,4,8,9-dibenzo-1,6-dioxaspiro[4.4]nonane-2,7-dione is an especially preferred member of the latter class.

The spirodilactam precursor is reacted according to the process of the invention with an aliphatically-unsaturated imido-primary amine, that is, an organic compound having one primary amino group, i.e., —NH$_2$ group, and one aliphatically-unsaturated imido group, as carbon atom substituents. While the process of the invention will take place with a variety of imido primary amines of varying structure, best results are obtained in the process of the invention if the imido and amino groups are not located on adjacent carbon atoms, that is, at least one atom, carbon or otherwise, separates the two carbon atoms on which the primary amino group and the aliphatically-unsaturated imido group are substituted. One class of such imido primary amines comprises imido primary amines of up to 30 carbon atoms inclusive, which are represented by the formula III

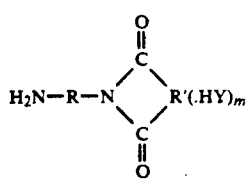

where R is a divalent organic radical of up to 30 carbon atoms inclusive and is divalent alkylene or divalent arylene of 1 or 2 aromatic rings which, when two rings are present, incorporates rings which are fused or which are connected by a link, X, wherein X is a direct valence bond, or X is alkylene of up to 8 carbon atoms inclusive, oxy, thio, sulfonyl, carbonyl, dioxyphenylene, 2,2-di(oxyphenyl)propane, di(oxyphenyl) sulfone, or dioxydiphenylene; m is 0 or 1; HY is an acid which forms a salt with the amine, including both inorganic and organic acids which do not interfere with the reaction, such as hydrohalogenic acids, e.g., hydrochloric and hydrobromic; sulfur acids, e.g., surfuric or sulfonic; phosphorus acids, e.g., phosphoric or phosphonic; and carboxylic acids, e.g., oxalic and the like. Preferably, Y is halogen, e.g., fluorine, chlorine, bromine or iodine and especially chlorine or bromine, with the proviso that the amino and imido groups are not located on adjacent carbon atoms. R is hydrocarbyl, that is, contains only atoms of carbon and hydrogen besides any other atoms in the link X, or is substituted hydrocarbyl containing additionally other atoms as inert, monovalent substituents on carbon atoms such as halo, preferably middle halo. R' is an aliphatically-unsaturated divalent aliphatic or alicyclic group of up to about 20 carbon atoms, and when alicyclic, of 1 to 2 rings. Aliphatically-unsaturated divalent organic radicals included by R' are, for example,

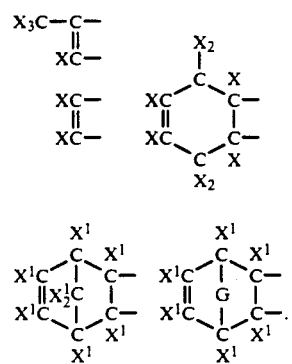

where G is —SO$_2$—, —S—, or —O—; and X' is a radical selected from hydrogen, lower alkyl, halogen, or mixtures thereof, such as chloro, methyl, ethyl, propyl, bromo, etc. In instances where the R' radicals have isolated double bonds which are not activated, a reduced rate of addition with the polyamine has been found to occur. This includes radicals disclosed in U.S. Pat. Nos. 3,740,378 and 4,851,501, the disclosures of which are incorporated herein by reference.

Illustrative aliphatically-unsaturated imido-primary amines include N-[4-(4-aminobenzyl)phenyl]-5-norbornene-2,3-dicarboximide, N-(2-aminoethyl)-maleimide, N-(4-aminophenyl)bromomaleimide, N-(4-aminocyclophexyl)citralonimide, N-(4-aminophenyl)-1,2,3,6-tetrahydrophthalimide, and the like. Preferably, the aliphatically-unsaturated imido-primary amine is one having a 5-norborneneyl group, such as N-[4(4-aminobenzyl)phenyl]-5-norbornene-2,3-dicarboximide or the like.

In the reaction mixture, the ratio of the imido-primary amine to the spirodilactam precursor is of importance. If an excess of the spirodilactam precursor is employed, a polymeric product such as that described in allowed copending U.S. patent application Ser. No. 245,432 filed Sept. 16, 1988 is likely to be obtained as the principal product. To obtain the monomeric product of the invention the molar ratio of imido primary amine to spirodilactam precursor should be greater than 2:1 and preferably up to about 8:1. The reaction is conducted in the liquid phase in the presence of a reaction diluent. Suitable reaction diluents are those which are inert to the reactants and product under reaction conditions and which will dissolve at least a portion of each reactant at reaction temperature. Such diluents include ethers, e.g., acyclic ethers such as diethylene glycol dimethyl ether and tetraethylene glycol dimethyl ether as well as cyclic ethers such as tetrahydrofuran and dioxolane, N-alkylamides such as N,N-dimethylacetamide and N-methyl-2-pyrrolidone, and sulfur-containing diluents such as dimethyl sulfoxide and sulfolane. It is particularly convenient to employ as a diluent, either alone or in combination with other diluents such as a material with which water forms an azeotrope. This procedure facilitates the reaction and allows the water by-product to be removed as a generally low-boiling azeotrope.

The reaction of the imido-primary amine and the spirodilactam precursor takes place in a suitable reactor under reaction conditions which will typically include a reaction temperature of from about 50° C. to about 250° C. but more often from about 100° C. to about 200° C. Suitable reaction pressures are sufficient to maintain the reaction mixture in a liquid phase, e.g., pressures from about 1 atmosphere to about 20 atmospheres. During the reaction period, the contact of the reactants is maintained by conventional methods such as stirring or refluxing and subsequent to reaction the product is recovered by well-known techniques such as solvent removal or precipitation.

The spirodilactam bisimide product of the invention is a 1,6-diaza[4.4]spirodilactam having an aliphatically-unsaturated imido-containing substituent on each of the spiro ring nitrogen atoms, which substituent is a residue of the imido-primary amine where the primary amino group has participated in spirodilactam production. In terms of the spirodilactam precursors (formulas I and II) and the imido primary amine reactant (formula III), the product is represented by the formula IV

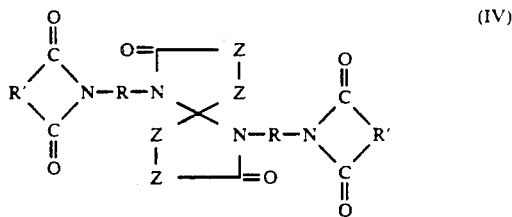
(IV)

wherein R, R' and Z have the previously stated meanings. The identity and nomenclature of such products will be apparent from consideration of the formulas for the reactants and product and the description of the reactants.

SPIRODILACTAM POLYAMINE OLIGOMER BISIMIDES

In the oligomerization reaction of the invention the spirodilactam precursor and the primary diamine react with an aliphatically-unsaturated aliphatic or alicyclic dicarboxylic acid compound which will suitably have two of the carboxy functions on non-adjacent carbon atoms as free carboxyl groups (—$CO_2H$ groups), as halides thereof or together as a linear anhydride moiety. A preferred class of acids comprises alicyclic or aliphatic dicarboxylic acid compounds having up to 30 carbon atoms in each acid compound and up to 2 rings, inclusive, including those represented by the formula V $HO_2C—R'—CO_2H$ (V)

wherein R' is an aliphatically-unsaturated aliphatic or alicyclic divalent group of up to 20 carbon atoms and from 1 to 2 rings. R' is preferably hydrocarbyl and can be substituted hydrocarbyl containing additional atoms as inert carbon atom substituents, e.g., halogen atoms and preferably the middle halogens, alkyl of 1 to 4 carbon atoms, and the like. As mentioned above, acid halides or anhydrides are also suitable acid compound reactants.

Illustrative of the aliphatic or alicyclic dicarboxylic acid compounds which are useful in the process of the invention include maleic acid, bromomaleic acid, citraconic acid, methyl-5-norbornene-2,3-dicarboxylic acid, methyl-tetrahydrophthalic acid, itaconic acid, exo-3,6-epoxy-1,2,3,6-tetrahydrophthalic acid, allylnadic acid, the corresponding anhydrides or acid halides and the like or any of the acids disclosed in U.S. Pat. Nos. 3,740,378 and 4,851,501, the disclosures of which are incorporated herein by reference. In general hydrocarbon R' groups are preferred as the reactant of formula IV, and particularly preferred are those where R' is alicyclic bond. Such dicarboxylic acid compounds of one bridged ring give best results, particularly norbornene-2,3-dicarboxylic acid.

The primary diamine is an organic compound having two primary amino groups, e.g., —$NH_2$ groups, as carbon atom substituents. While the process of the invention will take place with a variety of primary diamines of varying structure, best results are obtained in the process of the invention if the two amino groups are not located on adjacent carbon atoms, that is, at least one atom, carbon or otherwise, separates the two carbon atoms on which the primary amino groups are substituted. One class of such primary diamines comprises primary diamines of up to 30 carbon atoms inclusive which are represented by the formula VI $H_2N—R—NH_2$ (VI)

where R is a divalent organic radical of up to 30 carbon atoms inclusive and is divalent which, when two rings are present, incorporates rings which are fused or which are connected by a link, X, wherein X is a direct valence bond, alkylene of up to 8 carbon atoms inclusive, oxy, thio, sulfonyl, carbonyl, dioxyphenylene, 2,2-di(oxyphenyl)propane, di(oxyphenyl)sulfone, and dioxydiphenylene, with the proviso that the two amino groups are not located on adjacent carbon atoms. R is hydrocarbyl, that is, contains only atoms in the link X, or is substituted hydrocarbyl containing additionally other atoms as inert, monovalent substituents on carbon atoms such as halo, preferably middle halo.

Illustrative of alkylene-containing diamines of the above formula III are trimethylenediamine, tetramethylenediamine, hexamethylenediamine, octamethylenediamine, 1,7-diamino-4-methyloctane, 1,4-diaminocyclohexane, 1,10-diamino-5-chlorodecane and 1,6-diamino-3,4-diethylhexane. Arylene diamines of the above formula III include p-phenylenediamine, 2,4-toluenediamine, di(4-aminophenyl) ether, di(4-aminophenyl)methane, 2,2-di(3-amino-4-methylphenyl)propane, di(4-amino-2-ethylphenyl) sulfone, di(3-amino-4-chlorophenyl) ketone, di(2-aminophenyl) sulfide, 1,3-di(4-aminophenyloxy)benzene, 2,2-di[4-oxy(4-aminophenyl)phenyl]propane and 4,4'-di(4-aminophenyloxy)-biphenyl. The preferred primary diamines are those diamines of the above formula III wherein R is divalent arylene and is hydrocarbyl except for any additional atoms present in any X. Particularly preferred are the di(aminophenyl)alkanes such as di(4-aminophenyl)alkane or di(aminophenyl) ethers such as di(4-aminophenyl) ether or having a single aromatic ring, e.g., p-phenylenediamine.

The reaction of the spirodilactam precursor, the primary diamine and the dicarboxylic acid compound, is conducted in the liquid phase in the presence of an inert reaction diluent. Diluents which are liquid at reaction conditions and in which the reactants are at least partially soluble at reaction temperature are satisfactory. Suitable diluents include the N-alkylamides such as N,N-dimethylformamide, N,N-dimethylacetamide and N-methyl-2-pyrrolidone, phenols such as phenol and m-cresol, sulfur-containing diluents such as dimethylsulfoxide, sulfolane or the like.

The oligomerization is conducted by contacting the reactants in a suitable reactor under oligomerization conditions and maintaining reactant contact by conventional methods such as shaking or stirring. The relative properties of the reactants may vary within certain limits and the properties of the resulting oligomer vary accordingly. The molar ratio of spirodilactam precursor to dicarboxylic acid compound is suitably from about 10:1 to about 1:3 preferably will be from about 5:1 to about 1:2. As the primary diamine reacts with both the spirodilactam precursor and the dicarboxylic acid compound, the molar quantity of the primary diamine should preferably be about equal to the total molar quantity of the other two reactants. Molar ratios of primary diamine to total spirodilactam precursor plus dicarboxylic acid compound from about 1:1 to about 1:1.2 are satisfactory but molar ratios of from about 1:1 to about 1:1.05 are preferred.

The oligomerization is conducted at an elevated temperature. Reaction temperatures from about 80° C. to about 250° C. are suitable with preferred reaction temperatures being from about 120° C. to about 200° C. A suitable reaction pressure is one which will maintain the reaction mixture in a liquid phase. Such pressures are typically up to about 20 atmospheres but more often are from about 0.8 atmospheres to about 10 atmospheres. During reaction, any water present or formed is preferably removed by conventional procedures such as selective extraction or distillation, preferably azeotropic distillation with a portion of the reaction diluent or with a second reaction diluent with which water forms an azeotrope, e.g., toluene or ethylbenzene. Subsequent to reaction, the oligomer produced is recovered by conventional methods such as solvent removal, extraction or precipitation.

The oligomer produced is an aliphatically-unsaturated imido end-capped (terminated) polyamine containing amine linkages. The amine linkages result from spirodilactam moiety formation. The oligomer produced thus contains moieties of the non-amino portion of a primary diamine alternating with a 1,6-diaza [4.4] spirodilactam moiety connected to the remainder of the oligomer chain through the spiro ring nitrogen atoms and end-capped with an aliphatically-unsaturated imido moiety derived by the loss of hydroxyl groups or anhydride oxygen equivalents from reaction of the carboxy functions of the dicarboxylic acid compound with the primary diamine. In terms of the reactants as depicted above (formulas I or II, V and VI) the oligomers produced are represented by the repeating formula VII

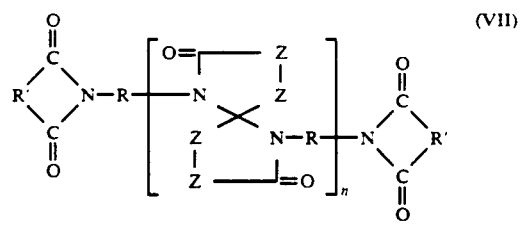

wherein Z, R, and R' have the previously stated meaning and n is from about 2 to 20, preferably from about 2 to about 10. Of particular interest are the oligomers of formula VII having a molecular weight from about 1,000 to about 40,000.

The nomenclature of the oligomer products of the formula VII is not easily determined because of the complexity thereof, but the identity of the products will be apparent from the above discussion of the reactants and consideration of the formula for the products as depicted above. Illustrative of such products is the oligomer illustratively produced from 4-oxoheptanedioic acid or 1,6-dioxaspiro[4.4]nonane-2,7-dione, di(4-aminophenyl)methane and cis-5-norbornene-endo-2,3-dicarboxylic anhydride, the oligomer produced from 2,3,5,6-tetramethyl-4-oxoheptanedioic acid or 3,4,8,9-tetramethyl-1,6-dioxaspiro[4.4]nonane-2,7-dione, p-phenylenediamine and maleic acid and the oligomer illustratively produced from di(2-carboxyphenyl)ketone or 3,4,8,9-dibenzo-1,6-dioxaspiro[4.4]nonane-2,7-dione, 2,2-di(4-aminophenyl)propane and anhydride. Preferred oligomer products are those of the above formula VII wherein Z is >C(Z')$_2$ in which Z' is hydrogen or methyl, R is divalent arylene, and R' is a norborn-5-ene-2,3-yl group.

CURED PRODUCTS

The spirodilactam bisimides and oligomers of forumulas IV and VII of the invention are difunctional aliphatically-unsaturated bisimides having a polycyclic central portion.

The bisimides of formulas IV and VII find utility as thermosetting resins which are employed in the production of cured or crosslinked products useful as surface coatings, in adhesives formulations and in fiber-reinforced composites wherein, for example, the reinforcing fiber is glass or carbon. Such products are produced by conventional methods. The cured products are also useful in the production of hollow objects as by filament winding and are employed as impregnating and casting resins.

The curing of the bisimides of formulas IV and VII is accomplished by conventional methods such as thermal or photochemical excitation, or by catalyzed polymerization employing cationic or anionic catalysts or free radical polymerization. Anionic polymerization uses alkali metal alcoholates, hydroxides, amides or the like as catalysts while typical cationic polymerization catalysts are inorganic or organic acids, are Lewis acids or the like. Such cationic catalysts include, sulfuric acid, phosphoric acid, p-toluenesulfonic acid, boron-trifluoride, tin tetrachloride and the like. Free radical polymerization catalysts include peroxides, such as benzoyl peroxide, acetyl peroxide and the like. Catalysts are generally employed in a quantity of from about 0.05% by weight to about 5% by weight, based on total composition.

In an alternate embodiment, the aliphatically-unsaturated spirodilactam derivatives are cured by heating with a substantial amount, e.g., from about 20% by weight to about 50% by weight, based on total curable composition, of a polyfunctional curing agent. Although a wide variety of conventional curing agents are usefully employed with the unsaturated spirodilactam derivatives, e.g., polyfunctional cyanato compounds or unsaturated isocyanurates, the preferred polyfunctional curing agents are the bis(maleimide) compounds such as described by Zahiret et al, U.S. Pat. No. 4,100,140. Bis(4-maleimidophenyl)methane is a particularly preferred polyfunctional curing agent.

The curing process is conducted by heating a mixture of the spirodilactam derivative and the curing agent to a temperature above about 150° C. but below about 300° C. It is frequently useful to conduct the heating in stages as by heating the compositon to be cured to a relatively low curing temperature to initiate the curing process and subsequently raise the temperature to a higher curing temperature to complete the cure. This process of curing in stages is conventional for the curing of thermoset resins. The curing can be conducted using a polar solvent, such as methyl ethyl ketone, methanol, ethanol or the like, which evaporates during the curing process.

ILLUSTRATIVE EMBODIMENTS

The invention is further illustrated by the following Illustrative Embodiments which should not be construed as limiting the invention.

ILLUSTRATIVE EMBODIMENT I

A mixture of 25.18 g (0.073 mole) of N-[4-(4-aminobenzyl)phenyl]5-norbornene-2,3-dicarboximide, 5.7 g (0.0365 mole) of 1,6-dioxaspiro[4.4]nonane-2,7-dione, and 50 ml of N-methyl-2-pyrrolidone was heated while being stirred to 170°-180° C. for 12 hours. The resulting mixture was cooled and poured into methanol. The precipitated product was dried in a vacuum oven at 80° C. for 24 hours. The product had a melting point of >250° C. and the nuclear magnetic resonsnace spectra were consistent with the structure 1,6-di[4-(4-aminophenylmethyl)phenyl-5-norborene-2,3-dicarboximide]-1,6-diaza[4.4]nonane-2,7-dione. Molding of the product at 250° C. for 3 minutes gave a cured material having a glass transition temeprature (Tg) >300° C.

ILLUSTRATIVE EMBODIMENT II

A mixture of methylene dianiline (10.0 g, 0.05 mole), 1,6-dioxaspiro[4.4]nonane-2,7-dione (7.09 g, 0.0454 mole), cis-5-norbornene-endo-2,3-dicarboxylic anhydride (1.65 g, 0.01 mole) and 50 ml 1-methyl-2-pyrrolidin-one is placed in a 250 ml round-bottomed flask equipped with a mechanical stirrer and a condensor and warmed with stirring to 170°-180° C. The temperature is maintained at this level for 12 hours. After cooling, the reaction mixture is poured into methanol and the precipitated resin product is dried in a vacuum oven at 80° C. for 24 hours. The resin product had a melting point of >250° C. and a nuclear magnetic resonance spectra consistent with the structure of a spirodilactam-based oligomer terminated with 5-norbornene2,3-dicarboximide groups. Molding of this resin product at 250° C. for 3 minutes gave a cured material showing TG >300° C.

What is claimed is:

1. The spirodilactam of the formula IV

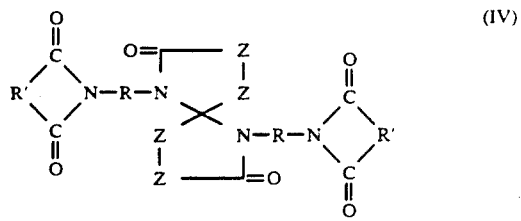

wherein R is a divalent organic radical of up to 30 carbon atoms selected from divalent alkylene or divalent arylene of 1 or 2 aromatic rings which, when two rings are present are fused or joined by X wherein X is a direct valence bond, alkylene of up to 8 carbon atoms inclusive, oxo, thio, sulfonyl, carbonyl, dioxyphenylene, 2,2-di(oxyphenyl)propane, di(oxyphenyl) sulfone or dioxydiphenylene; R' is the 5-norbornene-2,3-yl group shown below,

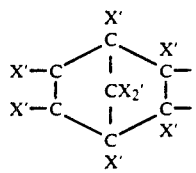

wherein X' is a radical selected independently from hydrogen lower alkyl or halogen, and Z independently is $>C(Z')_2$ in which Z' independently is hydrogen, lower alkyl, lower halo or phenyl.

2. The spirodilactam of claim 1 wherein each R is divalent arylene.

3. The spirodilactam of claim 2 wherein Z' is selected independently from hydrogen or lower alkyl.

4. The spirodilactam of claim 3 wherein Z' is hydrogen or methyl.

5. The spirodilactam of claim 4 wherein R is phenylenemethylphenyl.

6. The spirodilactam of claim 5 wherein Z' is hydrogen and R' is 5-norbornene-2,3-yl.

7. The spirodilactam of claim 4 wherein R is phenylene.

8. The spirodilactam of claim 7 wherein Z' is hydrogen.

* * * * *